(12) United States Patent
Buford et al.

(10) Patent No.: US 6,743,418 B1
(45) Date of Patent: Jun. 1, 2004

(54) DEODORANT PAD SYSTEM

(76) Inventors: Barbara Buford, 4554 S. Leamington, Chicago, IL (US) 60638; Brittney Buford, 4554 S. Leamington, Chicago, IL (US) 60638

( * ) Notice: Subject to any disclaimer, the term of this patent is extended or adjusted under 35 U.S.C. 154(b) by 85 days.

(21) Appl. No.: 10/093,132

(22) Filed: Mar. 5, 2002

Related U.S. Application Data

(60) Provisional application No. 60/273,409, filed on Mar. 6, 2001.

(51) Int. Cl.[7] .............................. A61K 7/32; A61K 7/00
(52) U.S. Cl. .......................... 424/65; 424/400; 424/401
(58) Field of Search .......................... 424/65, 400, 401

(56) References Cited

U.S. PATENT DOCUMENTS

| | | | |
|---|---|---|---|
| 4,534,962 A | 8/1985 | Marschner | |
| 4,817,790 A | * 4/1989 | Porat et al. | 424/401 |
| 5,324,490 A | 6/1994 | Van Vlahakis et al. | |
| 5,403,588 A | 4/1995 | Santa Ana, Jr. | |
| 6,444,214 B1 | * 9/2002 | Cole et al. | 424/401 |

* cited by examiner

*Primary Examiner*—Shelley A. Dodson
(74) *Attorney, Agent, or Firm*—Matthew J. Peirce

(57) ABSTRACT

A deodorant pad is disclosed. The deodorant pad would comprise a towelette which would be included within an aluminum foil package. Each towelette would be approximately two inches by two inches. Each towelette would be immersed in a solution of baby powder, baking soda, deodorant, and water. Because the towelette would be stored within the aluminum foil packet, the towelette would be capable of being stored for long periods of time until needed for use. The present invention would be transportable and would be disposable after use.

4 Claims, 1 Drawing Sheet

DEODORANT PAD SYSTEM

This application claims the benefit of provisional application No. 60/273,409 filed Mar. 6, 2001.

I. BACKGROUND OF THE INVENTION

The present invention concerns that of a new and improved deodorant pad.

II. DESCRIPTION OF THE PRIOR ART

U.S. Pat. No. 5,403,588, issued to Santa Ana, Jr., discloses a body deodorant composition which is incorporated into an absorbent cotton pad as a solution and packaged in individual pouches for use.

U.S. Pat. No. 5,324,490, issued to Van Vlahakis et al., discloses a perfumed stable gel and a deodorant container which retains a deodorant in the form of that perfumed stable gel and which is adapted for use with various deodorant dispensers.

U.S. Pat. No. 4,534,962, issued to Marschner, discloses a novel stable pituitous bicarbonate suspension in an queous/alcoholic medium having a high alcohol content and a low water content.

III. SUMMARY OF THE INVENTION

The present invention concerns that of a new and improved deodorant pad. The deodorant pad would comprise a towelette which would be included within an aluminum foil package. Each towelette would be approximately two inches by two inches. Each towelette would be immersed in a solution of baby powder, baking soda, deodorant, and water. Because the towelette would be stored within the aluminum foil packet, the towelette would be capable of being stored for long periods of time until needed for use. The present invention would be transportable and would be disposable after use.

There has thus been outlined, rather broadly, the more important features of a deodorant pad that the detailed description thereof that follows may be better understood and in order that the present contribution to the art may be better appreciated. There are, of course, additional features of the deodorant pad that will be described hereinafter and which will form the subject matter of the claims appended hereto.

In this respect, before explaining at least one embodiment of the deodorant pad in detail, it is to be understood that the deodorant pad is not limited in its application to the details of construction and to the arrangements of the components set forth in the following description or illustrated in the drawings. The deodorant pad is capable of other embodiments and being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present deodorant pad. It is important, therefore, that the claims be regarded as including such equivalent constructions insofar as they do not depart from the spirit and scope of the present invention.

It is therefore an object of the present invention to provide a deodorant pad which has all of the advantages of the prior art and none of the disadvantages.

It is another object of the present invention to provide a deodorant pad which may be easily and efficiently manufactured and marketed.

It is another object of the present invention to provide a deodorant pad which is of durable and reliable construction.

It is yet another object of the present invention to provide a deodorant pad which is economically affordable and available for the consumer market.

Other objects, features and advantages of the present invention will become more readily apparent from the following detailed description of the preferred embodiment when considered with the attached drawings and appended claims.

IV. BRIEF DESCRIPTION OF THE DRAWINGS

V. DESCRIPTION OF THE PREFERRED EMBODIMENT

Figure 1:
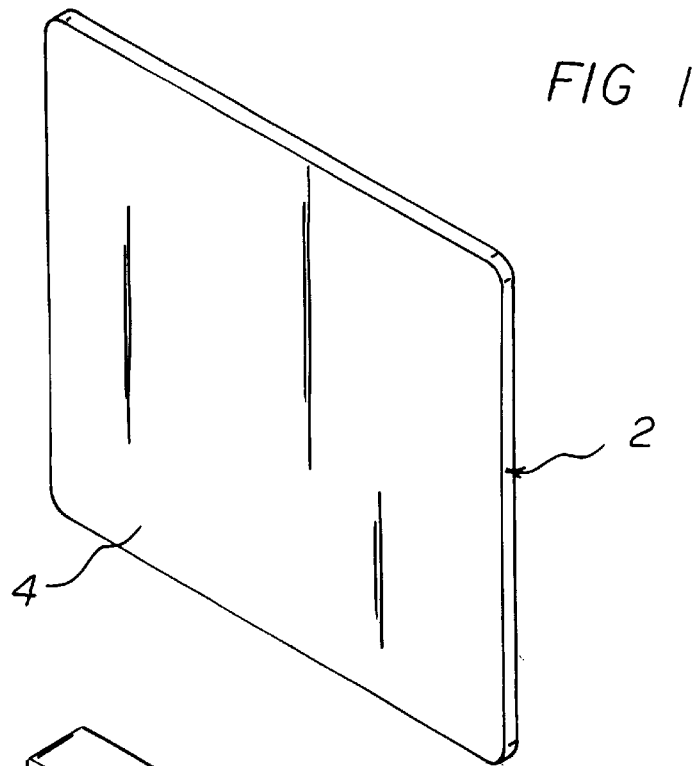
FIG. 1 shows a perspective view of the present invention.

FIG. 1 shows a perspective view of the present invention. The present invention concerns that of a new and improved deodorant pad 2. The deodorant pad 2 would comprise a towelette 4 which would be included within an aluminum foil package 6. Each towelette 4 would be approximately two inches by two inches. Each towelette 4 would be immersed in a solution of baby powder, baking soda, deodorant, and water. Because the towelette 4 would be stored within the aluminum foil packet 6, the towelette 4 would be capable of being stored for long periods of time until needed for use. The present invention would be transportable and would be disposable after use.

The amount of water that would be used with the present solution would be an amount that would not exceed one ounce of water, due to the size of the packet 6. To this volume of water would be added a pinch of baby powder, a pinch of baking soda, and a pinch of deodorant. A "pinch" is not quantitatively defined herein but would likely be an amount approximately equal to one-twentieth to one-tenth of a teaspoon due to the size of the packet.

Figure 2:
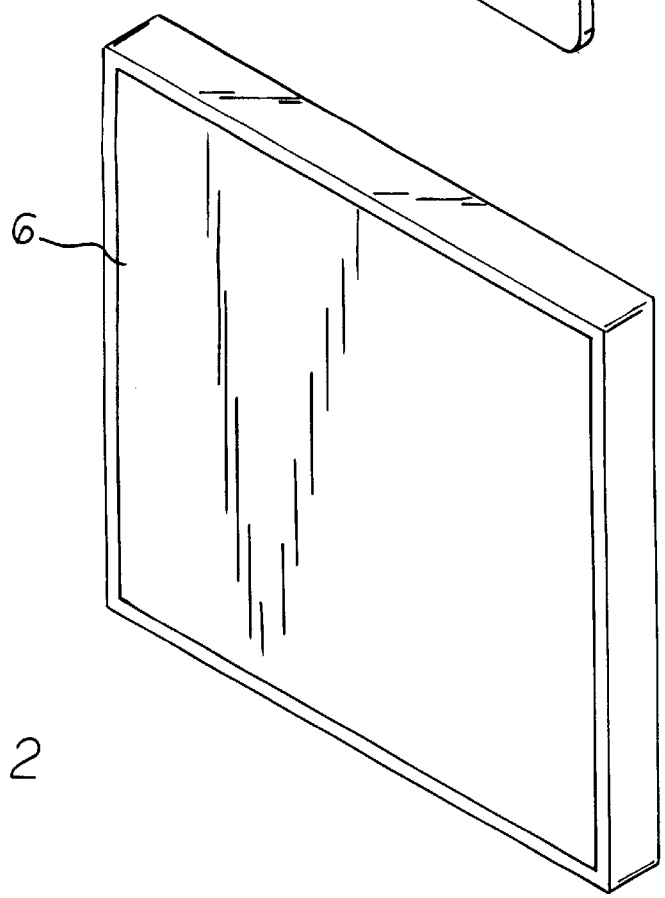
FIG. 2 shows an aluminum foil package of the present invention.

FIG. 2 shows an aluminum foil package 6 of the present invention. Due to the small size and compactness of the aluminum foil package 6, it can be easily transported in a purse, knapsack, fanny pack, or other small and convenient location. The towelette 4 of the present invention can be disposed after use.

What I claim as my invention is:

1. A deodorant pad system comprising:
   (a) a towelette, the towelette having a length of two inches by two inches,
   (b) a container for enclosing the towelette, the container being sealed,
   (c) a volume of deodorizing solution located within the container,
   (d) wherein the towelette would be immersed in the volume of deodorizing solution located within the container and would absorb some or all of the volume of deodorizing solution located within the container.

2. A deodorant pad system according to claim 1 wherein the towelette and the container would be disposable.

3. A deodorant pad system according to claim 2 wherein the container would be an aluminum foil package.

4. A deodorant pad system according to claim 2 wherein the volume of deodorizing solution located within the container would comprise up to an ounce of water, one-twentieth of a teaspoon to one-tenth of a teaspoon of baby powder dissolved in the water, one-twentieth of a teaspoon to one-tenth of a teaspoon of baking soda dissolved in the water, and one-twentieth of a teaspoon to one-tenth of a teaspoon of deodorant dissolved in the water.

* * * * *